United States Patent
Akkara et al.

(10) Patent No.: US 6,448,050 B1
(45) Date of Patent: *Sep. 10, 2002

(54) ENZYME-CATALYZED MODIFICATIONS OF MACROMOLECULES IN ORGANIC SOLVENTS

(75) Inventors: Joseph A. Akkara, Holliston, MA (US); Ferdinando F. Bruno, Andover, MA (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/639,412

(22) Filed: Aug. 14, 2000

Related U.S. Application Data

(60) Division of application No. 09/165,043, filed on Oct. 1, 1998, now Pat. No. 6,210,936, which is a continuation-in-part of application No. 08/774,329, filed on Nov. 27, 1996, now Pat. No. 6,063,916.

(51) Int. Cl.[7] .............................. C12P 7/62; C12P 21/00
(52) U.S. Cl. .................... 435/135; 536/123.1; 536/18.5; 536/58; 536/107; 536/115; 536/119; 536/124; 523/426
(58) Field of Search ....................... 435/135; 536/123.1, 536/18.5, 58, 107, 115, 119, 124; 523/426

(56) References Cited

U.S. PATENT DOCUMENTS

| 4,215,200 A | * | 7/1980 | Miyata et al. ............... 435/273 |
| 5,554,508 A | * | 9/1996 | Auriol et al. ............... 435/68.1 |
| 6,210,936 B1 | * | 4/2001 | Akkara et al. ............... 435/135 |

OTHER PUBLICATIONS

Santoyo–Gonzalez et al. "Selective pivaloylation and diphenylacetylation of cyclomalto–oligosaccharides." Carbohydrate Research, 262 (1994), pp. 271–282.*

* cited by examiner

*Primary Examiner*—Samuel Barts
*Assistant Examiner*—Devesh Khare
(74) *Attorney, Agent, or Firm*—Vincent J. Ranucci

(57) ABSTRACT

Protease enzyme from *Bacillus subtilis* and Bacillus sp. Catalyzes the acylation of organic solvent-insoluble macromolecules in isooctane solution containing vinyl esters of fatty acids, lactones or lactides as acyl donors. The reaction occurs only when the enzyme is solubilized via ion-pairing with the anionic surfactant dioctylsulfosuccinate, sodium salt (AOT). Enzyme based acylation was demonstrated in macromolecules such as silk proteins. These macromolecules are reactive either as cryogenically milled powder suspended in the organic solvent or as a thin film deposited onto ZnSe slides. This selective acylation approach represents the first attempt at using enzymes to modify organic-insoluble macromolecules in nonaqueous media.

19 Claims, 2 Drawing Sheets

FTIR spectra of control (SilkFilm) and derivatized silk proteins (SilkDerFilm)

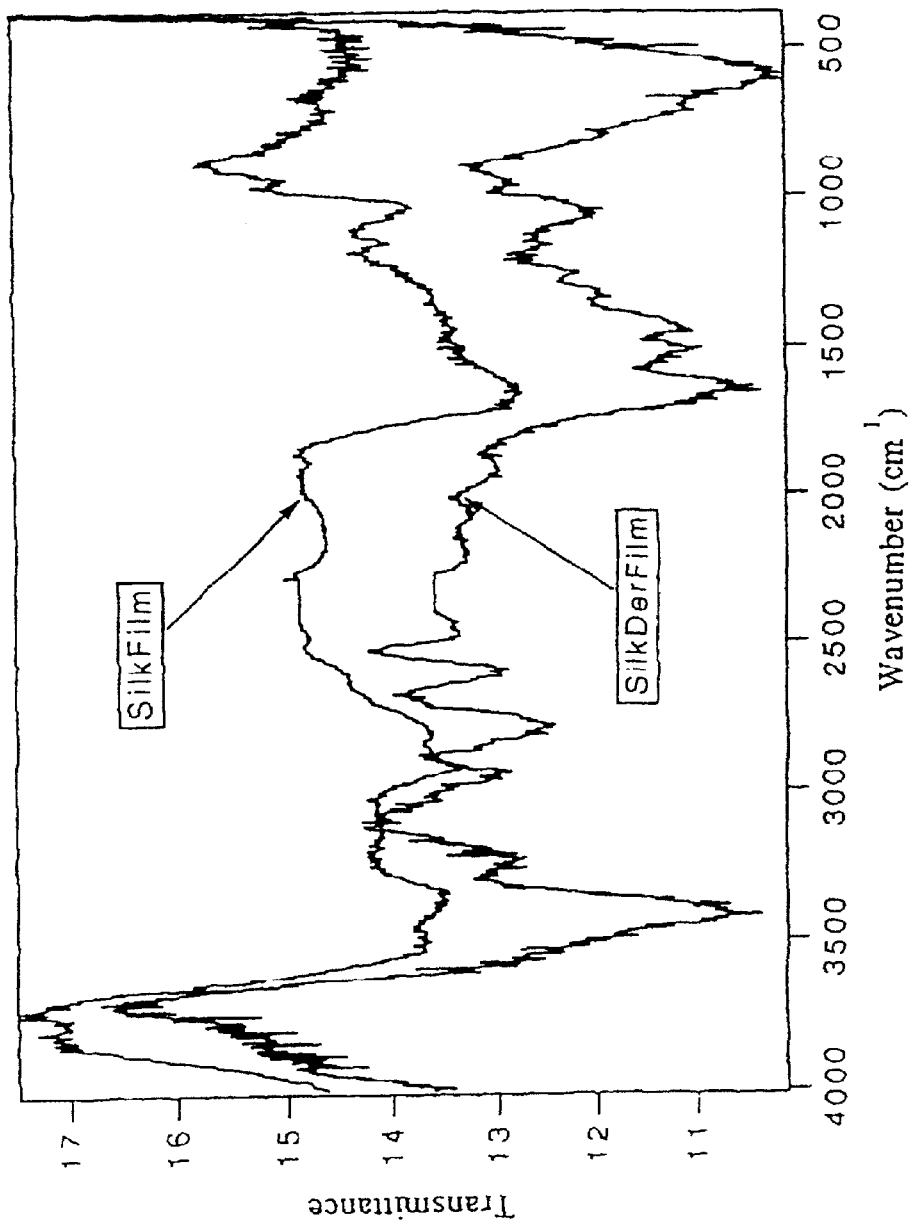
Figure 1 FTIR spectra of control (SilkFilm) and derivatized silk proteins (SilkDerFilm)

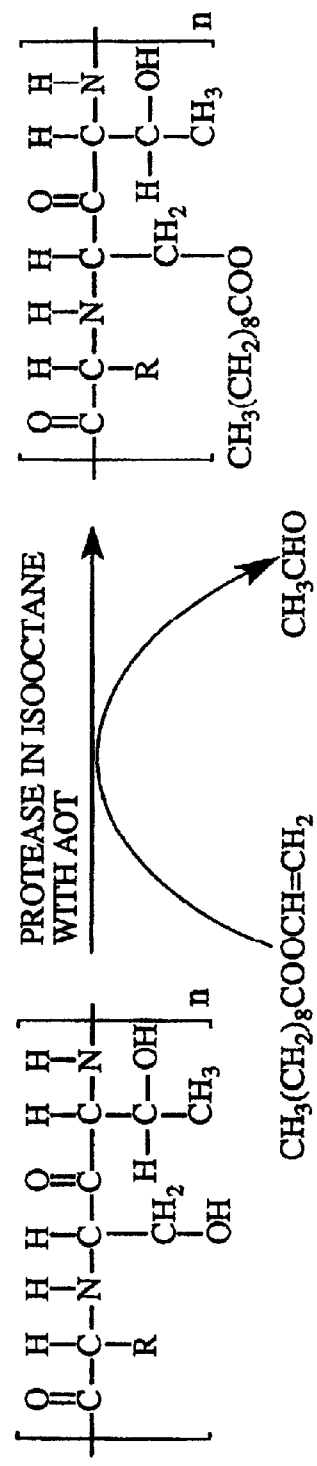
Fig. 2 Schematics for the esterification reaction of silk proteins by proteae enzyme in isooctane with AOT

ENZYME-CATALYZED MODIFICATIONS OF MACROMOLECULES IN ORGANIC SOLVENTS

CROSS-REFERENCE TO RELATED APPLICATION

This application is a division of application Ser. No. 09/165,043, filed Oct. 1, 1998, now U.S. Pat. No. 6,210,936, which is a continuation-in-part of U.S. patent application Ser. No. 08/774,329, filed Nov. 27, 1996, U.S. Pat. No. 6,063,916 in the name of Joseph A. Akkara et. al.

STATEMENT OF GOVERNMENT INTEREST

The invention described herein may be manufactured and used by the Government for government purposes without the payment of any royalty thereon.

FIELD OF THE INVENTION

The present invention relates generally to the enzyme-catalyzed modification of insoluble macromolecules in organic solvents.

BACKGROUND OF THE INVENTION

Selective modification of macromolecules is desirable to tailor their structural and functional properties, such as hydrophobicity, hydrophilicity, and interfacial and film forming properties. E.g., fatty acid esters of macromolecules may be useful as bioerodable and biodegradable drug delivery matrices such as coatings, finishes and films, and biodegradable emulsifiers, compatibilizers and detergents.1 However, selective acylation of hydroxylated macromolecules by chemical reactions are difficult due to multiple steps involved in the modification (protection, deprotection, extraction, separation and purification), and due to the lack of specificity, solubility and the presence of multifunctional groups in the polymer.2 Enzymes have been used to acylate saccharides of different glucose moieties regioselectively under mild condition in organic solvents. 2–4 Similar reactions with other hydroxylated macromolecules would be desirable. However, the lack of solubility of these polymers and the enzymes in organic solvents implies significant problems in carrying out these conversions. Accordingly, alternate methods of achieving a functionally significant degree of modifications are required.5–7

Enzymes are powerful catalysts in organic solvents where they catalyze a wide variety of reactions that are difficult to perform in aqueous solutions. This is particularly evident in esterification reactions catalyzed by lipases and proteases wherein a variety of nucleophiles act as substrates for enzyme-catalyzed acyl transfer in nearly anhydrous organic solvents. Unfortunately, many hydroxylated compounds are either sparingly soluble in only the most polar organic solvents, or are completely insoluble in organic media. For these substrates, conventional non-aqueous enzymology is unable to support catalytic transformations. The development of a suitable technique for the selective modification of macromolecules in organic solvents, therefore, would represent both an opportunity for the synthesis of novel materials as well as means to overcome a technical hurdle in the broader uses of enzymes in non-aqueous media.

Accordingly, it is an object of this invention to overcome the above illustrated inadequacies and problems of insoluble macromolecules by providing a improved method of their modification.

It is another object of this invention to provide a method of acylating hydroxylated macromolecules wherein their selective modification results in structural and/or functional benefits.

Yet another object of the present invention is to provide a method of enabling the use of enzymes to catalyze reactions in non-aqueous media for the synthesis of biodegradable, bioerodable and biocompatible compounds.

SUMMARY OF THE INVENTION

The present invention provides process for the production of esterified polyhydroxylated macromolecules such as proteins, where the esterification is limited to alcohols of serine, threonine and hydroxyproline present at the surface of the proteins. Such attributes are novel because chemical esterification is unable to modify selectively such macromolecules. The processes also emphasize the use of mild reaction conditions such as temperature, pressure and pH, recycling of the reaction media leading to waste minimization, minimal by product formation, and minimal separations and purifications. Reaction media and the catalysts can be easily regenerated to minimal product cost and environmental hazard. Since the reactions are carried out at ambient conditions and selectively, the biological activity of the macromolecules such as enzyme activity and binding affinity are retained even after esterification.

Recently, a method was developed to solubilize enzymes in hydrophobic organic solvents through the formation of enzyme-surfactant ion pairs.8 These ion-paired, organic-soluble enzymes are extremely active in hydrophobic solvents, such as isooctane. The present invention demonstrates that hydroxylated macromolecules such as silk proteins, collagen, xanthan gum, hyaluronic acid, polyvinyl alcohol and polyethylene glycol when deposited as thin film or cryogenically milled can be selectively acylated by catalysis in organic solvents using an organic-soluble enzyme preparation of subtilisin (from *Bacillus subtilis*). This represents the first attempt at catalyzing solvent-insoluble macromolecular modification using enzymes in organic solvents.

Proteases such as subtilisin (from *Bacillus subtilis*), ion paired with AOT, remained predominantly active and soluble in isooctane, To enhance the reactivity of insoluble substrates, thin layers and cryogenically milled powders of hydroxylated macromolecules such as silk proteins, collagen, xanthan gum hyaluronic acid, polyvinyl alcohol and polyethylene glycol were prepared to increase the surface area and some of these biopolymers and synthetic polymers were selectively esterified using ion-paired proteases.

Modified macromolecules can be used for biodegradable emulsifiers, bioerodable films, coatings and fibers, hydrogels, compatibilizers and detergents. Of particular importance is the potential use of these low cost polymers for edible wrapping films utilized for food storage. In addition to the above applications, esterified macromolecules can be of extreme interest to the paper industry in order to efficiently recycle paper and other compounds based on cellulose. Since the reactions are carried out selectively using mild conditions, biological activities of these macromolecules may be enhanced by changing their transport and binding affinities. Another application that can be envisioned in the manufacturing of drug delivery systems as hydrogels (pH, temperature and pressure sensitive), specific filters, high absorbance compounds, coatings, finishes, films, fibers and membranes.

Other objects, features and advantages will be apparent from the following detailed description of preferred embodiments thereof taken in conjunction with the accompanying drawings.

BRIEF DESCRIPTION OF THE DRAWINGS

FIG. 1 shows the FTIR spectra of control and derivatized silk proteins;

FIG. 2 shows proposed schematics for the esterification reaction of silk proteins prepared by protease catalysis in isooctane containing AOT.

DETAILED DESCRIPTION OF EMBODIMENTS

The enzymatic process described herein can be envisioned as a new method for the selective modification of hydroxylated macromolecules in nonaqueous media, even when the macromolecule is insoluble in the organic solvent. This approach is amenable to a wide range of enzymes and acyl donors. Moreover this technique is capable to derivatize hydroxylated polymers such as silk proteins, xanthan gum, collagen, hyaluronic acid, polyvinyl alcohol and polyethylene glycol. Preparatory to experimental verification of the present invention, *Bacillus subtilis* (1.1 mg/mL, Protease N or Protease S) was dissolved in N-[2-hydroxyethyl] piperazine-N'-[2-ethanesulfonic acid] (HEPES) or 1,3-bis[tris(hydroxymenthyl)-methylamino]propane (BTP) buffer (10 mM, pH 7.8) containing 6 mM KCl. The aqueous solution was mixed with an equal volume of isooctane containing 2 mM dioctysulfosuccinate, sodium salt (AOT) and the biphasic solution at 250 C. was stirred at 250 rpm. After 30 minutes the phases were allowed to separate and the organic phase was removed.8 The protein and the water content of the isooctane solution were determined by absorbance at 280 nm and Karl-Fischer titration, respectively. Based on the measurements, approximately 1.0 mg/mL of enzyme was in the isooctane solution with a water content of <0.01%. This enzyme solution in isooctane containing AOT was used for acylation of macromolecules described below.

As an example for the formation of the thin layer of the macromolecule, 10 mg of the silk proteins were suspended in 100 mL of boiling water. The solution was poured in a beaker where was placed a ZnSe slide. The water was dried out by evaporation and the polymers were deposited onto ZnSe slide (2.54 cm×2.54 cm×0.1 mm) as a thin layer (estimated thickness 1000. The acylation was then performed, as set forth in the example below.

EXAMPLE 1

An isooctane solution (containing the enzyme and AOT) that contained a 40-fold molar excess of vinyl ester [In-capric vinyl ester (C10VE), n-caproic vinyl ester (C6VE), or n-butyric vinyl ester (C4VE)] or lactone [ε-caprolactone (ECL), γ-caprolactone (GCL), γ-butyrolactone (GBL) or δ-valerolactone (DVL)] relative to the macromolecules' hydroxyl groups, was pipetted onto a thin layer of nonacylated macromolecules deposited onto ZnSe slides. The reaction was allowed to proceed in the absence of shaking for 72 hours at 37° C. at which time it was terminated by removing the solid polymer and washing it with fresh isooctane to remove unreacted vinyl ester, lactone, AOT and the enzyme.

EXAMPLE 2

The transesterification was also conducted using cryogenically milled macromolecules. A similar procedure as used for the thin layer form, above, was used for the powder form, except that the reaction was performed in the presence of shaking (350 rpm). Here silk proteins are reported as an example. The protein powder has a particle size less than 100 mm. The surface area to weight ratio was 546 cm2/g. The enzymatic esterification reaction was initiated by adding 60 mM of the vinyl fatty acid [n-capric vinyl ester (C10VE), n-caproic vinyl ester (C6VE), or n-butyric vinyl ester (C4VE)]; lactone [[ε-caprolactone (ECL), γ-caprolactone (GCL), γ-butyrolactone (GBL) or δ-valerolactone (DVL)] or lactides [(3S) cis-3,6-dimethyl-1,4-dioxane-2,5-dione] to the isooctane solution containing AOT and solubilized protease (Protease N or Protease S) and the macromolecule in the powder form.

Results

The products were dried overnight and used for analytical assessment. Fourier Transform Infrared (FTIR) spectra of the films were collected on a FTIR Raman 7600 and the number of scans were 6400.

The results for enzymatic modification of silk proteins illustrates the general principles of the present invention. As shown in FIG. 1, the enzymatic reaction resulted in transesterification of silk proteins with an FTIR spectrum that contained large absorption peaks at 3000 cm−1 (corresponding to the C—H stretch of an alkyl chain) and a leak in the region of 1693–1737 cm−1, corresponding to a C=O of an ester group.

In control experiments, this type of carbonyl peak was not present in the unmodified silk proteins in the thin film form or when the silk proteins were treated with fatty acid esters in the absence of enzyme. It is also important to note that when Protease was used as a catalyst without ion pairing, no acylation occurred. Thus, the soluble enzyme form in the presence of AOT is required for acylation of the insoluble macromolecules. Moreover, no vinyl group was present in the modified silk proteins as determined by the lack of absorbance at 871 and 951 cm−1 in the FTIR spectrum Thus, absorption of the vinyl esters to the protein during the reaction does not occur.

Superscripted reference numerals have been used throughout the preceding text to indicate reference sources. Those numerals correspond to the following references.

1. Mayer, J. M.; Kaplan, D. L.; 2 Trends Polym. Sci., 227 (1994).
2. Klibanov, A. M.; 14 Trends Biochem. Sci., 141 (1989).
3. Klibanov, A. M.; 23 Acc. Chem. Res., 114 (1990).
4. Dordick, J.S.; 11 Enzyme Micro. Technol., 194 (1989).
5. Kuhl, P.; Haling, P. J.; Jakubke, H. D.; 31 Tetrahedron Lett., 5213 (1990).
6. Gill, I.; Vulfson, E.; 115 J. Am. Chen. Soc., 3348 (1994).
7. Bruno, F. F.; Akkara, J. A.; Kaplan, D. L.; Gross, R.; Swift, G.; Dordick, J. S.; 28 Macromolecules, 8881 (1995).
8. Paradkar, V. M.; Dordick, J. S.; 116 J. Am. Chem. Soc., 5009 (1994).

It will now be apparent to those skilled in the art that other embodiments, improvements, details and uses can be made consistent with the letter and spirit of the foregoing disclosure and with the scope of this patent, which is limited only by the following claims, construed in accordance with patent law, including the doctrine of equivalents.

What is claimed is:

1. A method of esterifying organic solvent-insoluble macromolecules by enzymatic catalysis, the method comprising the steps of:

(a) solubilizing an enzyme in a volume of hydrophobic organic solvent provided with a surfactant by formation of enzyme-surfactant ion pairs, (b) initiating an esterification reaction by addition to the volume of hydrophobic organic solvent containing the solubilized enzyme of (i) a macromolecule to be esterified having at least one hydroxyl group available for esterification and (ii) a molar excess, relative to the number of macromolecule hydroxyl groups available for esterification, of an acyl group donor reagent, (c) allowing the esterification reaction to continue under incubation conditions, and (d) terminating the esterification reaction by washing the macromolecule with a volume of fresh hydrophobic organic solvent to remove any unreacted acyl reagent, wherein the macromolecule is selected from the group consisting of xanthan gum and hyaluronic acid.

2. A method, as claimed in claim 1, wherein the macromolecule to be esterified is deposited on an inert substrate as a thin film.

3. A method, as claimed in claim 1, wherein the macromolecule to be esterified is a cryogenically milled powder.

4. A method, as claimed in claim 1, wherein the enzyme is a protease.

5. A method, as claimed in claim 4, wherein the enzyme protease is from *Bacillus subtilis*.

6. A method, as claimed in claim 4, wherein the enzyme protease is from Bacillus sp.

7. A method, as claimed in claim 1, wherein the hydrophobic solvent is isooctane.

8. A method, as claimed in claim 1, wherein the acyl donor group reagent is selected from the group consisting of vinyl esters.

9. A method, as claimed in claim 8, wherein the acyl group donor reagent is selected from the group consisting of n-capric vinyl ester, n-caproic vinyl ester and n-butyric vinyl ester.

10. A method, as claimed in claim 1, wherein the acyl donor group reagent is selected from the group consisting of lactones and lactides.

11. A method, as claimed in claim 10, wherein the acyl group donor reagent is selected from the group consisting of ε-caprolactone, γ-caprolactone, γ-butyrolactone, δ-valerolactone and (3S) cis-3,6-dimethyl-1,4-dioxane-2,5-dione.

12. A method, as claimed in claim 1, wherein the macromolecule to be esterified is selectively acylated.

13. An esterified organic solvent-insoluble macromolecule, made by:

(a) solubilizing an enzyme in a volume of hydrophobic organic solvent provided with a surfactant by formation of enzyme-surfactant ion pairs, (b) initiating an esterification reaction by addition to the volume of hydrophobic organic solvent containing the solubilized enzyme of (i) a macromolecule to be esterified having at least one hydroxyl group available for esterification and (ii) a molar excess, relative to the number of macromolecule hydroxyl groups available for esterification, of an acyl group donor reagent, (c) allowing the esterification reaction to continue under incubation conditions, and (d) terminating the esterification reaction by washing the macromolecule with a volume of fresh hydrophobic organic solvent to remove any unreacted acyl donor group reagent, wherein the macromolecule is selected from the group consisting of xanthan gum and hyaluronic acid.

14. An esterified organic solvent-insoluble macromolecule, as claimed in claim 13, wherein the macromolecule to be esterified is deposited on an inert substrate as a thin film.

15. An esterified organic solvent-insoluble macromolecule, as claimed in claim 13, wherein the macromolecule to be esterified is cryogenically milled powder.

16. An esterified organic solvent-insoluble macromolecule, as claimed in claim 13, wherein the enzyme is a protease.

17. An esterified organic solvent-insoluble macromolecule, as claimed in claim 13, wherein the enzyme is a protease from *Bacillus subtilis*.

18. An esterified organic solvent-insoluble macromolecule, as claimed in claim 13, wherein the enzyme is a protease from Bacillus sp.

19. An esterified organic solvent-insoluble macromolecule, as claimed in claim 13, wherein the hydrophobic solvent is isooctane.

* * * * *